US006197340B1

(12) United States Patent
Byrd et al.

(10) Patent No.: US 6,197,340 B1
(45) Date of Patent: *Mar. 6, 2001

(54) CONTROLLED RELEASE LIPOIC ACID

(75) Inventors: Edward A. Byrd, San Francisco, CA (US); Rajiv Janjikhel, Owings Mills, MD (US)

(73) Assignee: Medical Research Institute, Aptos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/288,245

(22) Filed: Apr. 8, 1999

Related U.S. Application Data

(63) Continuation-in-part of application No. 09/112,623, filed on Jul. 9, 1998, now abandoned.
(60) Provisional application No. 60/102,605, filed on Oct. 1, 1998, and provisional application No. 60/087,203, filed on May 28, 1998.

(51) Int. Cl.$^7$ ................................................. A61K 9/22
(52) U.S. Cl. ..................... 424/468; 424/451; 424/452; 424/457; 424/463; 424/464; 424/465; 424/474; 424/475; 424/489; 424/490; 424/400
(58) Field of Search ..................... 424/400, 480, 424/488, 494; 514/560, 45 L, 464, 400, 465, 472, 473, 486, 451, 457, 463, 468, 474, 475, 489, 490

(56) References Cited

U.S. PATENT DOCUMENTS

| 3,577,551 | 5/1971 | Murakami et al. . |
| 4,705,867 | 11/1987 | Giray et al. . |
| 4,800,044 | 1/1989 | Giray et al. . |
| 4,966,732 | 10/1990 | Giray et al. . |
| 5,334,612 | 8/1994 | Kalden et al. . |
| 5,376,382 | 12/1994 | Goede et al. . |
| 5,455,264 | 10/1995 | Beisswenger et al. . |
| 5,527,539 | 6/1996 | Sarlikiotis et al. . |
| 5,532,269 | 7/1996 | Koltringer . |
| 5,569,670 | 10/1996 | Weischer et al. . |
| 5,599,835 | 2/1997 | Fischer . |
| 5,650,429 | 7/1997 | Conrad et al. . |
| 5,691,379 | 11/1997 | Ulrich et al. . |
| 5,693,664 | 12/1997 | Wessel et al. . |
| 5,705,192 | 1/1998 | Bethge et al. . |
| 5,728,735 | * 3/1998 | Ulrich et al. ................... 514/560 |
| 5,730,988 | 3/1998 | Womack . |
| 5,827,643 | 10/1998 | Conrad et al. . |

FOREIGN PATENT DOCUMENTS

| 1 668 887 | 7/1971 | (DE) . |
| 36 29 116 A1 | 3/1988 | (DE) . |
| 42 20 851 A1 | 1/1993 | (DE) . |
| 43 17 646 A1 | 12/1994 | (DE) . |
| 43 38 508 A1 | 5/1995 | (DE) . |
| 43 43 592 A1 | 6/1995 | (DE) . |
| 43 43 647 A1 | 6/1995 | (DE) . |
| 44 00 269 A1 | 7/1995 | (DE) . |
| 44 47 599 A1 | 7/1996 | (DE) . |
| 0 159 519 | 2/1987 | (EP) . |
| 0 702 953 A2 | 8/1995 | (EP) . |
| 0 733 363 A1 | 3/1996 | (EP) . |
| 0 712 574 A2 | 10/1996 | (EP) . |
| 60-184011 | 9/1985 | (JP) . |
| WO 98/57627 | 12/1998 | (WO) . |

OTHER PUBLICATIONS

Armstrong et al., *Free Radical Biology and Chemistry*, (1996) 21(5):719–726.
Barbiroli et al., *J Neurol*, (1995) 242:472–477.
Baur et al., *Klin Wochenschr*, (1991) 69:722–724.
Bilich et al., *I–Pharmacodynamics*, (1978) 88:93.
Black et al., *Clinical and Experimental Pharmacology and Physiology*, (1998) 25:712–714.
Bloomgarden, *Diabetes Care*, (Apr. 1997) 20(4):670–673.
Burkart et al., *Agents Actions*, (1993) 38:60–65.
Busse et al., *Arzneim–Forsch/Drug Research* (1992) 42(6):829–831.
Bustamante et al., *Free Radical Biology and Medicine*, (1998) 24(6):1023–1039.
Carreau, *Methods in Enzymology*, (1979) 62:152–158.
Cesolari et al., *Rev Exp Enf Ap Digest*, (1988) 73(3) 229–232.
Chen et al., *Archives of Biochemistry and Biophysics*, (1997) 338(2):165–172.
Devasgayam et al., *Chem–Biol Interactions*, (1993) 86:79–92.
Dimpfel et al., *Dev Pharmacol Ther*, (1990) 14:193–199.
Egan et al., *Prostaglandins*, (1978) 16(6):861–869.
Estrada et al., *Diabetes*, (Dec. 1996) 45:1798–1804.
Faust et al., *J. Immunopharmac*, (1994) 16(1):61–66.
Fuchs et al., *Skin Pharmacol*, (1994) 7:278–284.
Gandhi et al., *J Biosci*, (Sep. 1985) 9 (1 & 2):117–127.
Garrett et al., *Neuroscience Letters*, (1997) 222:191–194.
Gerbitz et al., *Diabetes*, (Feb. 1996) 45:113–126.
Hammarqvist et al., *Crit Care Med*, (1997) 25(1):78–84.
Haugaard et al., *Biochem Biophys Acta*, (1970) 222:583–586.
Henricksen et al., *American Physiological Society*, (1990) C648–C653.
Henricksen et al., *Life Sciences*, (1997) 61(8):805–812.

(List continued on next page.)

Primary Examiner—Thurman K. Page
Assistant Examiner—Charesse L. Evans
(74) Attorney, Agent, or Firm—Karl Bozicevic Bozicevic, Field & Francis LLP

(57) ABSTRACT

A controlled release formulation of lipoic acid is disclosed. The lipoic acid is combined with excipient materials in such a way that those materials protect the lipoic acid from chemical degradation in the gastrointestinal tract and provide for gradual release of the lipoic acid. These combined features make it possible to use lipoic acid to reduce serum glucose levels and maintain those levels over time thereby obtaining a range of desired results.

20 Claims, No Drawings

OTHER PUBLICATIONS

Hofmann et al., *Archives of Biochemistry and Biophysics*, (1995) 324(1):85–92.
Jacob et al., *Diabetes*, (1995) 245–250.
Jacob et al., *Diabetes*, (Aug. 1996) 45:1024–1029.
Kagan et al., *Biochemical Pharmacology*, (1992) 44(8):1637–1649.
Kagan et al., *Journal of Lipid Research*, (1992) 33:385–397.
Kagan et al., *Free Rad Res Comms*, (1991) 15(5):265–276.
Khamaisi et al., *Metabolism*, (Jul. 1997) 45(7):763–768.
Lavis et al., *The Journal of Biologic Chemistry*, (Jan. 10, 1970) 245(1):23–31.
Lodge et al., *Journal of Applied Nutrition*, (1997) 49 (1 & 2)3–11.
Lodge et al., *Free Radical Biology & Medicine*, (1998) 25(3):287–297.
Matsugo et al., *Biochemistry and Molecular Biology International*, (Oct. 1995) 37(2)375–383.
Merin et al., *FEBS Letters*, (1996) 294:9–13.
Muller et al., *Toxicology*, (1989) 58:175–185.
Muller et al., *Biochimica et Biophysica Acta*, (1990) 1052:386–389.
Muller et al., *Journal of Cerebral Blood Flow and Metabolism*, (1995) 15:624–630.
Nagamatsu et al., *Diabetes Care*, (1995) 18(8):1160–1167.
National Diabetes Data Group Classification and Diagnosis of Diabetes Mellitus and Other Categories of Glucose Intolerance, *Diabetes* (1979) 28:1039–1057.
Natraj et al., *J. Biosci*, (1984) 6(1):38–46.
Nickander et al., *Free Radical Biology & Medicine* (1996) 21(5):631–639.
Ohmori et al., *Japan J. Pharmacol*, (1986) 42:275–280.
Ohmori et al., *Japan J. Pharmacol*, (1986) 42:135–140.
Ou et al., *Free Rad Res*, (1996) 25(4):337–346.
Ou et al., *Biochemial Pharmacology*, (1995) 50(1):123–126.
Packer et al., *Free Radical Biology & Medicine*, (1997) 22(1/2):359–378.
Packer et al., *Free Radical Biology & Medicine*, (1995) 19(2):227–250.
Packer, *Diabetologica*, (1993) 36:1212–1213.
Pascoe et al., *Free Radical Biology & Medicine*, (1989) 6:209–224.
Peinado et al., *Archives of Biochemistry and Biophysics*, (Sep. 1989) 273(2):389–395.
Podda et al., *Biochemical Pharmacology*, (1996) 52:627–633.
Prehn et al., *Journal of Cerebral Blood Flow and Metabolism* (1992) 12:78–87.
Reed et al., *Science*, (1951) 93–94.
Roy et al., *Biochemical Pharmacology*, (1997) 53:393–399.
Scheer et al., *Archives of Biochemistry and Biophysics*, (May 1, 1993) 302(2):385–390.
Schmid et al., *FASEB Journal*, (Jul. 1998) 12:863–870.
Schonheit et al., *Biochimica et Biophysica Acta*, (1995) 1271:335–342.
Segermann et al., *Arzneim.–Forsch./Drug Res.*, (1991) 41(12):1294–1298.
Sen et al., *The FASEB Journal*, (May 1996) 10:709–720.
Sen et al., *Free Radical Biology & Medicine*, (1997) 22(7):1241–1257.
Sen et al., *Biochemical and Biophysical Research Communications* (1998) 247:223–228.
Simopoulos, *Nutrition Today*, (Jan./Feb. 1994) 12–16.
Stoll et al., *Pharmacology Biochemistry and Behavior*, (1993) 46:799–805.
Streeper et al., *American Physiological Society*, (1997) 273(1):E185–E191.
Sumathi et al., *Jpn J Med Sci Biol*, (1996) 49:39–48.
Suzuki et al., *Free Rad Res Commsii*, (1992) 17(3):211–217.
Suzuki et al., *Biochemical and Biophysical Research Communications,*, (Dec. 1992) 189(3):1709–1715.
Suzuki et al., *Free Rad Res Comms*, (1991) 15(5) 255–263.
Szabo et al., *Klin Wochenschr*, (1986) 64(Suppl. VII):116–122.
Teichert et al., *Methods in Enzymology*, (1997) vol. 279.
Wagh et al., *J. Biosci*, (Mar. 1987) 11(1):59–74.
Wagh et al., *J. Biosci*, (Jun. 1986) 10(2):171–179.
Wagner et al., *Properties and Derivatives of α–Lipoic Acid*, (Oct. 5, 1956) 5079–5081.
Wickramasinghe et al., *Biochemical Pharmacology*, (1992) 43(3) 407–411.
Witt et al., *Journal of Chromatography B*, (1998) 705:127–131.
Wolz et al., *Nerupharmacology*, (1996) 35(3):369–375.
Ziegler et al., *Deutsche Medizinische Wochenschritt*, (Jul. 1, 1988) 113(26) 1071–1074.
Ziegler et al., *Diabetologia*, (1995) 38:1425–1433.
Zimmer et al., *J Mol Cell Cardiol*, (1995) 27:1895–1903.

* cited by examiner

CONTROLLED RELEASE LIPOIC ACID

CROSS-REFERENCE TO RELATED APPLICATIONS

This application is a continuation-in-part of earlier filed provisional patent application Serial No. 60/102,605, filed Oct. 1, 1998 and patent application Ser. No. 09/112,623, filed Jul. 9, 1998, which is the converted patent application of provisional patent application Serial No. 60/087,203, filed May 28, 1998 to which we claim priority under 35 U.S.C. §120 and §119(e) each of which is incorporated herein by reference in their entirety.

FIELD OF THE INVENTION

The invention relates generally to a controlled release oral formulation of pharmaceutically active compounds. More particularly the invention relates to controlled release lipoic acid oral formulations.

BACKGROUND OF THE INVENTION

A compound known as α-lipoic acid was first isolated by Reed and coworkers as an acetate replacing factor. It is slightly soluble in water, and soluble in organic solvents. α-lipoic acid is a chiral molecule and is known by a variety of names, including thioctic acid; 1,2-diethylene-3 pentanoic acid; 1,2-diethylene-3 valeric acid; and 6,8-thioctic acid. α-lipoic acid was tentatively classified as a vitamin after its isolation, but it was later found to be synthesized by animals and humans. The complete enzyme pathway that is responsible for the de novo synthesis has not yet been definitively elucidated. Several studies indicate that octanoate serves as the immediate precursor for the 8-carbon fatty acid chain, and cysteine appears to be the source of sulfur. As a lipoamide, it functions as a cofactor in the multienzyme complexes that catalyze the oxidative decarboxylation of α-keto acids such as pyruvate, α-keto glutarate, and branched chain α-keto acids.

More recently, a great deal of attention has been given to possible antioxidant functions for α-lipoic acid, and its reduced form, dihydrolipoic acid (DHLA). Lipoate, or its reduced form, DHLA, reacts with reactive oxygen species such as superoxide radicals, hydroxyl radicals, hypochlorous acid, peroxyl radicals, and singlet oxygen. It also protects membranes by interacting with vitamin C and glutathione, which may in turn recycle vitamin E. In addition to its antioxidant activities, DHLA may exert prooxidant actions to reduction of iron. α-lipoic acid administration has been shown to be beneficial in a number of oxidative stress models such as ischemia-reperfussion injury (IRI), diabetes (both α-lipoic acid and DHLA exhibit hydrophobic binding to proteins such as albumin, which can prevent glycation reactions), cataract formation, HIV activation, neurodegeneration, and radiation injury. Furthermore, lipoate can function as a redox regulator of proteins such as myoglobin, prolactin, thioredoxin, and NF-κB transcription factor.

Lipoate may also have other activities. For example, DHLA has been found in vitro to be an anti-inflammatory agent which at the same time interferes with nitric oxide release from inflammatory macrophages and protects target cells from oxygen radical attack. V. Burkhart, *Dihydrolipoic Acid Protects Pancreatic Islet Cells from Inflammatory Attack,* Agents Actions 38:60 (1993). This document, and all other documents cited to herein, is incorporated by reference as if reproduced fully herein.

Lipoic acid is a coenzyme for several enzymes. Lipoic acid is a coenzyme for both α-keto acid dehydrogenase complex enzymes (i.e. pyruvate dehydrogenase complex and α-keto glutarate dehydrogenase complex), branched chain α-keto acid dehydrogenase complex, and the glycine cleavage system. In the enzyme system, the body forms a multi-enzyme complex involving lipoic acid, that breaks down molecules of pyruvate produced in earlier metabolism, to form slightly smaller, high energy molecules, called acetyl-coenzyme A. This results in molecules that can enter into a series of reactions called the citric acid cycle, or Krebs cycle, which finishes the conversion of food into energy. Essentially, lipoic acid stimulates basal glucose transport and has a positive effect on insulin stimulated glucose uptake.

SUMMARY OF THE INVENTION

An oral formulation of lipoic acid is disclosed which formulation is comprised of lipoic acid and one or excipient materials. The ratio of lipoic acid to excipient material and the particular excipients used result in a formulation which protects the lipoic acid from degradation after oral administration and allows the lipoic acid to be released in a controlled manner for absorption into the circulatory system. By protecting the lipoic acid from degradation and maintaining a desired serum level of lipoic acid in blood serum the oral formulation of the invention achieves physiological effects which are superior to those which might be obtained when higher serum levels are obtained for a short term with an unformulated oral dosage or a single dose injectable formulation. By providing for controlled release of lipoic acid the physiological effects are continually provided over a period of time resulting in reduced glucose levels and A1c levels and thereby obtaining a range of associated health benefits. The controlled release formulation of the invention shows that highly desirable therapeutic effects can be obtained by continually maintaining a substantially constant lipoic acid blood serum level over long periods of time (4 or more hours) and maintain such day after day. Although the blood serum levels of lipoic acid could be at higher levels, desired results are obtained when those levels are maintained below the level previously thought to be needed to obtain therapeutic results.

An aspect of the invention is an oral formulation of lipoic acid, and excipient compounds which provide for controlled release.

A more specific aspect of the invention is that the formulation protects lipoic acid from degradation and allow it to be slowly released over time.

An advantage of the invention is that by maintaining relatively low serum levels of lipoic acid over long periods of time serum glucose levels are suppressed over long periods thereby inhibiting adverse effects which result from abnormally high serum glucose levels.

Another advantage of the invention is that by administering the formulation over long periods the patient is provided with a reduced risk of developing insulin resistance and/or diabetes mellitus.

Another aspect of the invention is that the formulation provides a method of treating type 2 diabetes, i.e. non-insulin-dependent diabetes mellitus (NIDDM).

Yet another aspect of the invention is that the lipoic acid may be present as a racemic mixture or with the R–(+) enantiomer present in amounts greater than 50% and constituting up to 100% of lipoic acid in the formulation.

An advantage of the invention is that a convenient oral delivery dosage form is used to obtain the results which are superior to a single dose injectable.

Another advantage of the invention is that glucose levels can be reduced and be maintained at levels substantially below levels without treatment via the present invention.

A feature of the invention is that the oral formulation may be a tablet, capsule, caplet, etc. containing any desired amount of lipoic acid.

Another aspect of the invention is that it may be formulated with one or more additional antidiabetic agents e.g. sulfonylureas; biguanides and thiazolidinediones.

Another aspect of the invention is a method of treatment whereby sustained low levels of lipoic acid blood serum over long periods continually stimulate basal glucose transport.

These and other objects, aspects, advantages, and features of the invention will become apparent to those persons skilled in the art upon reading the details of the invention as more fully described below.

DETAILED DESCRIPTION OF THE INVENTION

Before the present, formulations, methods and components used therein are disclosed and described, it is to be understood that this invention is not limited to particular compounds, excipients or formulations as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided are subject to change if it is found that the actual date of publication is different from that provided here.

DEFINITIONS

The term "lipoic acid" is intended to mean α-lipoic acid which is a chiral molecule also known as thioctic acid; 1,2-diethylene-3 pentanoic acid; 1,2-diethylene-3 valeric acid; and 6,8-thioctic acid. Unless specified the term covers the racemic mixture as well as any other (non-50/50) mixture of the enantiomers including substantially pure forms of either the R–(+) or the S–(–) enantiomer. Further, unless specified otherwise the term covers pharmaceutically acceptable salts (e.g. Na and K salts) and amides, esters and metabolites of the acid. The molecule formula is $C_8H_{14}O_2S_2$ the molecular weight is 206.32 and it has a pKa of 4.7. In referring to pharmaceutically acceptable salts the term is intended to encompass a conventional term of pharmaceutically acceptable acid addition salts which refer to salts which retain the biological effectiveness and properties of the free-base form of the acid and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malconic acid, succinic acid, maleic acid, fumaric, tartaric acid, citric acid, benzoic acid, cinnamic acid, mandelic acid, methanesulfonic acid, ethanesulfonic acid, p-toluenesulfonic acid, salicylic acid and the like. The same is true with respect to amides, esters and metabolites that is those forms which can be formed and maintain biological effectiveness and not have significant undesirable biological properties.

The term "excipient material" is intended to mean any compound forming a part of the formulation which is intended to act merely as a carrier i.e. not intended to have biological activity itself.

The term "chemical degradation" is intended to mean that the lipoic acid active ingredient is subjected to a chemical reaction which disrupts its biological activity.

The terms "treating", and "treatment" and the like are used herein to generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. arresting it's development; or (c) relieving the disease, i.e. causing regression of the disease and/or it's symptoms or conditions. The invention is directed towards treating patient's suffering from disease related abnormally high levels of glucose and are related to the effects of free radicals and/or oxidizing agents over long periods of time. The present invention is involved in preventing, inhibiting, or relieving adverse effects attributed to high levels of serum glucose over long periods of time and/or are such caused by free radicals or oxidizing agents present in a biological system over long periods of time.

The terms "synergistic", "synergistic effect" and the like are used interchangeably herein to describe improved treatment effects obtained by combining controlled release lipoic acid formulations of the invention with one or more other orally effective diabetic compounds. Although a synergistic effect in some fields means an effect which is more than additive (e.g., one plus one equals three) in the field of treating diabetes and related diseases an additive (one plus one equals two) or less than additive (one plus one equals 1.6) effect may be synergistic. For example, if a patient has an abnormally high glucose level, e.g. 400 mg/dl, that patient's glucose level might be reduced to 300 mg/dl by the conventional orally effective antidiabetic compound. Further, at a different time the same patient with a glucose level of 400 mg/dl might be administered a different orally effective antidiabetic compound which compound reduced the patient's glucose levels from 400 to 300 mg/dl. However, if both orally effective antidiabetic compounds are administered to the patient one would not ordinarily expect an additive effect thereby obtaining a reduction to 200 mg/dl and may obtain no more of a reduction in glucose level than when either drug is administered by itself. If additive effects could always be obtained then diabetes could be readily treated in all instances by coadministering several different types of orally effective antidiabetic compounds. However, such has not been found to be an effective treatment. However, in connection with the present invention coadministration of formulations of controlled release lipoic acid of the invention can be coadministered with other orally effective antidiabetic compounds in order to improve the effects which are synergistic, i.e. greater than the effects obtained by the administration of either composition by itself.

FORMULATION IN GENERAL

The formulation of the invention is preferably an oral dosage formulation which may be in any suitable oral form including tablets, capsules, caplets, suspensions, etc. The dosage may be of any desired size in terms of the lipoic acid active ingredient. However, sizes in a range of about 50 mg to about 1,000 mg are generally used, preferably 100 mg to 500 mg and more preferably about 300 mg. The amount a patient will need to obtain an optimum therapeutical effect will vary with a number of factors known to those skilled in the art e.g. the size, age, weight, sex and condition of the patient. The patient may begin with daily doses of about 300 mg and determine if glucose levels are reduced to acceptable levels. If the desired results are not obtained in one week the daily dosage amount can be increased in increments of 100 to 300 mg/day up to any useful amount e.g. 2,000 mg/day.

The manufactured compound α-lipoic generally exists as a 50/50 or racemic mixture of R–(+)-α-lipoic acid and S–(–)-α-lipoic acid. The R–(+) enantiomer is the naturally produced biological form of the compound and as such is believed to be largely responsible for obtaining the physiological effect. Thus, the active ingredient of the formulation of the present invention may be 100% R–(+) enantiomer. However, the active ingredient may be present in any mix of the two enantiomers e.g. 10% S–(–) and 90% R–(+); 25% S–(–) and 75% R–(+). Further, it should be noted that even though the R–(+) enantiomer is believed to be the more active the S–(–) enantiomer may possess unique properties which make inclusion of the S–(–) enantiomer important in any formulation used in treatment. Unless stated otherwise information disclosed here refers to formulations containing a racemic mixture. If the active ingredient is not a racemic mixture then some adjustment may be needed in the formulation in order to account for the greater activity of the R–(+) enantiomer as well as the slightly longer half life of the R–(+) enantiomer compared to the S–(–) enantiomer.

A typical formulation contains about 50–70% by weight lipoic acid active ingredient with the remainder being excipient material. Preferably the formulation comprises 55% to 65% active ingredient and more preferably about 60% active ingredient by weight. Thus, a particularly preferred oral formulation of the invention comprises about 300 mg of lipoic acid and about 200 mg of excipient material. Human patients generally eat during the day and sleep at night. Eating causes increased glucose levels. Accordingly, it is generally preferable to give a larger dose of lipoic acid at the beginning of the day. This may include two 300 mg tablets or a single 600 mg tablet. Later in the day the patient will take an additional 300 mg for a typical daily dose of about 900 mg for a 70 kg man.

The formulation is characterized by (a) protecting the active ingredient from chemical degradation in a patient's gastrointestinal tract and (b) releasing the active ingredient in a controlled manner. By gradually releasing the active ingredient the serum levels of lipoic acid obtained are (1) lower than those obtained with single dose injectable or a non-controlled release formulation; and (2) maintained over longer periods of time than obtained with single dose injectable or a non-controlled release formulation. Specifically, a formulation of the invention releases active ingredient so as to obtain a blood serum level in a human patient in a range of about 25 to 75 ng/ml of plasma. The range is preferably about 35 to 65 ng/ml of plasma and more preferably about 50 ng/ml of plasma ±5%.

One aspect of the invention is that a range of highly desirable therapeutic effects are obtained even when the lipoic acid blood serum levels are maintained in a range well below those previous used. The present invention could obtain desired therapeutics effects with higher levels of lipoic acid in blood serum. However, at least minimum levels would need to be constantly maintained over a long period of time (4 hours or more per day) for a plurality of days to obtain the desired results.

The lipoic acid blood plasma level is obtained via the present invention is insufficient to obtain a desired therapeutic effect if that level is maintained for only a short period of time e.g. 4 hours or less. However, by using the controlled release formulation of the invention these lower lipoic acid blood plasma levels can be maintained over 8 hours or more, preferably over 12 hours or more and more preferably over 16 hours or more per day. Further, those lipoic acid blood plasma levels over these periods of time are repeatedly obtained over a period of days, preferably weeks or months and more preferably continuously over any period during which the patient would benefit from reduced serum glucose levels—which may be the remainder of the patient's life.

To obtain the desired results a formulation of the invention needs to start with a sufficient amount of lipoic acid such that it is capable of releasing enough lipoic acid per unit of time to obtain the desired lipoic acid serum levels while compensating for lipoic acid which is metabolized. To obtain the desired results the formulation may provide an initial release of lipoic acid quickly and thereafter provide a gradual release which slows over the useful life of the formulation. However, the release may be gradual from the beginning. In either case there is a gradual slowing of the rate of release which is compensated for in that some of the previously released lipoic acid remains in the blood serum unmetabolized.

A preferred oral formulation is a tablet which is designed to dissolve gradually over a period of about 8 hours. As the tablet dissolves its reduced size will release smaller and smaller amounts of lipoic acid per unit of time. At the end of the 8 hours another tablet is administered and the process is repeated. To obtain the benefits of the invention the process is continually repeated over a plurality of days, weeks, months or years. By maintaining a minimal lipoic acid blood serum level over time a patient's abnormally high serum glucose levels are reduced and the long term adverse effects of elevated serum glucose levels are avoided.

COMBINATION FORMULATIONS

Lipoic acid acts directly on muscle cells to stimulate glucose transport. The effect on serum glucose reduction obtained with lipoic acid may be sufficient for some patients. However, if an insufficient glucose lowering effect results the lipoic acid may be supplemental with one or more orally effective antidiabetic agents selected from the group consisting of sulfonylureas, biguanides and thiazolidiones. Useful sulfonylureas include tolbutamide and glipizide and related compounds such as Amaryl, Pandin and Starlix. These drugs target pancreatic beta cells and stimulate these cells to release insulin. The biguanides include compounds such as metformin, phenformin and buformin. These compounds act on the liver to decrease hepatic glucose output and on the intestine to block glucose uptake into the blood. Thiazolidinediones include compounds such troglitazone, rosaglutazone and pioglitazone. These compounds are believed to sensitize muscle and fat cells to insulin.

Although all or any orally effective antidiabetics can be formulated with or administered along with the formulation of the invention it is preferable to administer metformin (particularly metformin Hydrochloride tablets sold as Glucophage®) with controlled release lipoic acid formulations of the invention. Some particularly preferred formulations include 300 mg lipoic acid and 500 mg of metformin hydrochloride or if a larger dose is needed 600 mg of lipoic acid and 1,000 mg of metformin hydrochloride. Additional enhanced effects may be obtained by taking lipoic acid with vitamin C and/or vitamin E. For example a patient might take 900 mg/day of lipoic acid 1,000 to 3,000 mg/day of vitamin C and 400 to 800 mg/day of vitamin E.

Example 10 provides specific examples of patient'swhich underwent coadministration of controlled release lipoic acid formulations of the present invention in combination with other treatments conventionally used to lower serum glucose levels. The synergistic effects were obtained, i.e. the combination of lipoic acid controlled release formulations of the invention with other therapeutic agents obtained results which were greater than results which might be expected with the administration of either composition by itself.

EXCIPIENT MATERIAL

Examples provided here show that formulations of the invention may comprise different amounts and ratios of active ingredient and excipient material. Further, different excipients can be used. Particularly preferred excipients and amounts used are recited in the Examples. However, upon reading the disclosure those skilled in the art will come to understand the general concepts of the invention and will recognize that other excipients, amounts, ratios and combinations might be used to obtain the results first shown here.

The type and amount of excipient material is added to obtain a formulation with two important characteristics. First, the resulting formulation protects the active ingredient from chemical degradation in the patient'sgastrointestinal tract. A formulation of pure, unprotected lipoic acid is not part of the scope of the present invention in that pure lipoic acid is degraded to some degree in the gastrointestinal tract. Although the formulation need not protect 100% of the lipoic acid from degradation to come within the scope of the invention it should protect at least 90% or more, preferably 95% or more and more preferably 99% or more of the lipoic acid from degradation. Although multiple doses of an oral formulation could be taken it is preferable to design the dosage such that a single dose is taken at each dosing event—preferably three times a day and more preferably twice a day. The better the active ingredient is protected from degradation the less active ingredient is needed in the original dosage thereby reducing manufacturing costs and increasing profits. The formulation must protect at least as much of the dose as is needed to obtain a pharmacological effect and preferably obtain the desired treatment results, e.g. maintaining a desired lipoic acid serum level needed to obtain a reduced serum glucose level over time.

The second necessary characteristic of the formulation is that it does not release all of the active ingredient at one time but rather releases the active ingredient gradually over time at a controlled rate of release which rate is preferably constant over 4 hours or more. This is particularly important because (1) lipoic acid has a relatively short half life and (2) a desired level of lipoic acid in blood serum must be maintained over a long period to obtain the desired effect. If all of the lipoic acid is released at once it will all enter the circulatory system at once and be metabolized in the liver thereby causing the lipoic acid serum level to drop below the desired level. When this occurs the effect on reducing glucose levels is suboptimal.

TYPICAL FORMULATIONS

A typical formulation of the invention will contain about 50% to 70% by weight of lipoic acid and a particularly preferred formulation will comprise 60% by weight of lipoic acid. Assuming a formulation with 60% by weight of lipoic acid with the remaining 40% being excipient material there are a number of possible components which could be used to make up that 40%. A generalized and specific description of such is provided below:

| | | |
|---|---|---|
| (1) | lipoic acid | 60% |
| | organic polymer | 40% |
| | TOTAL | 100% |
| (2) | lipoic acid | 60% |
| | organic polymer | 34.5% |
| | inorganics | 5.5% |
| | TOTAL | 100% |
| (3) | lipoic acid | 60% |
| | organic polymer | 30%–40% |
| | inorganics | 10% or less |
| | TOTAL | 100% |
| (4) | lipoic acid | 60% |
| | microcrystalline cellulose | 14% |
| | cellulose acetate phthalate aqueous dispersion | 15% |
| | polyvinylpyraolidone | 3% |
| | ethyl acetate | 2.5% |
| | hydrous magnesium silicate (talc) | 1% |
| | carboxy methyl ether | 4% |
| | magnesium stearate | 0.5% |
| | TOTAL | 100% |
| (5) | lipoic acid | 60% |
| | microcrystalline cellulose | 10–30% |
| | cellulose acetate phthalate aqueous dispersion | 5–25% |
| | polyvinylpyraolidone | 1–5% |
| | ethyl acetate | 1–5% |
| | hydrous magnesium silicate (talc) | 0.5–3% |
| | carboxy methyl ether | 1–5% |
| | magnesium stearate | 0.5–1.5% |
| | TOTAL | 100% |
| (6) | lipoic acid | 60% |
| | microcrystalline cellulose, NF (Avicel PH 101) | 14% |
| | Aquacoat CPD-30 (30% solids w/w) | 15% |
| | Plasdone K29/32, USP | 3% |
| | Carbopol 974P, NF | 2.5% |
| | Talc, USP | 1.0% |
| | croscarmellose sodium, NF (Ac, di-Sol) | 4.0% |
| | Magnesium Stearate, NF | 0.5% |
| | TOTAL | 100% |
| (7) | lipoic acid | 60% |
| | microcrystalline cellulose, NF (Avicel PH 101) | 10–30% |
| | Aquacoat CPD-30 (30% solids w/w) | 5–25% |

| -continued | |
|---|---|
| Plasdone K29/32, USP | 1–5% |
| Carbopol 974P, NF | 1–5% |
| Talc, USP | 0.5–3% |
| croscarmellose sodium, NF (Ac, di-Sol) | 1–5% |
| Magnesium Stearate, NF | 0.5–1.5% |
| TOTAL | 100% |

Those skilled in the art will recognize that there are endless possibilities in terms of formulations. Even if the formulations are limited to the relatively few compounds shown above the formulation could be changed in limitless ways by adjusting the ratios of the components to each other. The important feature of any formulation of the invention is that the lipoic acid be released gradually over 4 hours or more, preferably 8 hours or more. Some general types of controlled release technology which might be used with the present invention is described below followed by specific preferred formulations.

CONTROLLED RELEASE TECHNOLOGY

Controlled release within the scope of this invention can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms*, 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications*, 1980 (CRC Press, Inc.).

Controlled release drug delivery systems may also be categorized under their basic technology areas, including, but not limited to, rate-preprogrammed drug delivery systems, activation-modulated drug delivery systems, feedback-regulated drug delivery systems, and site-targeting drug delivery systems.

In rate-preprogrammed drug delivery systems, release of drug molecules from the delivery systems "preprogrammed" at specific rate profiles. This may be accomplished by system design, which controls the molecular diffusion of drug molecules in and/or across the barrier medium within or surrounding the delivery system. Fick's laws of diffusion are often followed.

In activation-modulated drug delivery systems, release of drug molecules from the delivery systems is activated by some physical, chemical or biochemical processes and/or facilitated by the energy supplied externally. The rate of drug release is then controlled by regulating the process applied, or energy input.

In feedback-regulated drug delivery systems, release of drug molecules from the delivery systems may be activated by a triggering event, such as a biochemical substance, in the body. The rate of drug release is then controlled by the concentration of triggering agent detected by a sensor in the feedback regulated mechanism.

In a site-targeting controlled-release drug delivery system, the drug delivery system targets the active molecule to a specific site or target tissue or cell. This may be accomplished, for example, by a conjugate including a site specific targeting moiety that leads the drug delivery system to the vicinity of a target tissue (or cell), a solubilizer that enables the drug delivery system to be transported to and preferentially taken up by a target tissue, and a drug moiety that is covalently bonded to the polymer backbone through a spacer and contains a cleavable group that can be cleaved only by a specific enzyme at the target tissue.

While a preferable mode of controlled release drug delivery will be oral, other modes of delivery of controlled release compositions according to this invention may be used. These include mucosal delivery, nasal delivery, ocular delivery, transdermal delivery, parenteral controlled release delivery, vaginal delivery, and intrauterine delivery.

There are a number of controlled release drug formulations that are developed preferably for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems*, 1992 (Marcel Dekker, Inc.). some of these formulations will now be discussed in more detail.

Enteric coatings are applied to tablets to prevent the release of drugs in the stomach either to reduce the risk of unpleasant side effects or to maintain the stability of the drug which might otherwise be subject to degradation of expose to the gastric environment. Most polymers that are used for this purpose are polyacids that finction by virtue or the fact that their solubility in aqueous medium is pH-dependent, and they require conditions with a pH higher then normally encountered in the stomach.

One preferable type of oral controlled release structure is enteric coating of a solid or liquid dosage form. Bnteric coatings promote the lipoates' remaining physically incorporated in the dosage form for a specified period when exposed to gastric juice. Yet the enteric coatings are designed to disintegrate in intestinal fluid for ready absorption. Delay of the lipoates' absorption is dependent on the rate of transfer through the gastrointestinal tract, and so the rate of gastric emptying is an important factor. Some investigators have reported that a multiple-unit type dosage form, such as granules, may be superior to a single-unit type. Therefore, in a preferable embodiment, the lipoates may be contained in an enterically coated multiple-unit dosage form. In a more preferable embodiment, the lipoate dosage form is prepared by spray-coating granules of an lipoate-enteric coating agent solid dispersion on an inert core material. These granules can result in prolonged absorption of the drug with good bioavailability.

Typical enteric coating agents include, but are not limited to, hydroxypropylmethylcellulose phthalate, methacryclic acid-methacrylic acid ester copolymer, polyvinyl acetate-phthalate and cellulose acetate phthalate. Akihiko Hasegawa, *Application of solid dispersions of Nifedipine with enteric coating agent to prepare a sustained-release dosage form*, Chem. Pharm. Bull. 33: 1615–1619 (1985). Various enteric coating materials may be selected on the basis of testing to achieve an enteric coated dosage form designed ab initio to have a preferable combination of dissolution time, coating thicknesses and diametral crushing strength. S. C. Porter et al., *The Properties of Enteric Tablet Coatings Made From Polyvinyl Acetate-phthalate and Cellulose acetate Phthalate*, J. Pharm. Pharmacol. 22:42p (1970).

On occasion, the performance of an enteric coating may hinge on its permeability. S. C. Porter et al., *The Permeability of Enteric Coatings and the Dissolution Rates of Coated Tablets*, J. Pharm. Pharmacol. 34: 5–8 (1981). With such oral drug delivery systems, the drug release process may be initiated by diffusion of aqueous fluids across the enteric coating. Investigations have suggested osmotic driven/rupturing affects as important release mechanisms from enteric coated dosage forms. Roland Bodmeier et al., *Mechanical Properties of Dry and Wet Cellulosic and Acrylic Films Prepared from Aqueous Colloidal Polymer Dispersions used in the Coating of Solid Dosage Forms*, Pharmaceutical Research, 11: 882–888 (1994).

Another type of useful oral controlled release structure is a solid dispersion. A solid dispersion may be defined as a dispersion of one or more active ingredients in an inert carrier or matrix in the solid state prepared by the melting (fusion), solvent, or melting-solvent method. Akihiko Hasegawa, *Super Saturation Mechanism of Drugs from Solid Dispersions with Enteric Coating Agents*, Chem. Pharm. Bull. 36: 4941–4950 (1998). The solid dispersions may be also called solid-state dispersions. The term "coprecipitates" may also be used to refer to those preparations obtained by the solvent methods.

Solid dispersions may be used to improve the solubilities and/or dissolution rates of poorly water-soluble lipoates. Hiroshi Yuasa, et al., *Application of the Solid Dispersion Method to the Controlled Release Medicine. III. Control of the Release Rate of Slightly Water-Soluble Medicine From Solid Dispersion Granules*, Chem. Pharm. Bull. 41:397–399 (1993). The solid dispersion method was originally used to enhance the dissolution rate of slightly water-soluble medicines by dispersing the medicines into water-soluble carriers such as polyethylene glycol or polyvinylpyraolidone, Hiroshi Yuasa, et al., *Application of the Solid Dispersion Method to the Controlled Release of Medicine. IV. Precise Control of the Release Rate of a Water-Soluble Medicine by Using the Solid Dispersion Method Applying the Difference in the Molecular Weight of a Polymer*, Chem. Pharm. Bull. 41:933–936 (1993).

The selection of the carrier may have an influence on the dissolution characteristics of the dispersed drug because the dissolution rate of a component from a surface may be affected by other components in a multiple component mixture. For example, a water-soluble carrier may result in a fast release of the drug from the matrix, or a poorly soluble or insoluble carrier may lead to a slower release of the drug from the matrix. The solubility of the lipoates may also be increased owing to some interaction with the carriers.

Examples of carriers useful in solid dispersions according to the invention include, but are not limited to, water-soluble polymers such as polyethylene glycol, polyvinylpyraolidone, or hydroxypropylmethyl-cellulose. Akihiko Hasegawa, *Application of Solid Dispersions of Nifedipine with Enteric Coating Agent to Prepare a Sustained-release Dosage Form*, Chem. Pharm. Bull. 33: 1615–1619 (1985).

Alternate carriers include phosphatidylcholine. Makiko Fujii, et al., *The Properties of Solid Dispersions of Indomethacin, Ketoprofen and Flurbiprofen in Phosphatidylcholine*, Chem. Pharm. Bull. 36:2186–2192 (1988). Phosphatidylcholine is an amphoteric but water-insoluble lipid, which may improve the solubility of otherwise insoluble lipoates in an amorphous state in phosphatidylcholine solid dispersions. See Makiko Fujii, et al., *Dissolution of Bioavailibility of Phenytoin in Solid Dispersion with Phosphatidylcholine*, Chem. Pharm. Bull 36:4908–4913 (1988).

Other carriers include polyoxyethylene hydrogenated castor oil. Katsuhiko Yano, et al., *In-Vitro Stability and In-Vivo Absorption Studies of Colloidal Particles Formed From a Solid Dispersion System*, Chem. Pharm. Bull 44:2309–2313 (1996). Poorly water-soluble lipoates may be included in a solid dispersion system with an enteric polymer such as hydroxypropylmethylcellulose phthalate and carboxymethylethylcellulose, and a non-enteric polymer, hydroxypropylmethylcellulose. See Toshiya Kai, et al., *Oral Absorption Improvement of Poorly Soluble Drug Using Soluble Dispersion Technique*, Chem. Pharm. Bull. 44:568–571 (1996). Another solid dispersion dosage form include incorporation of the drug of interest with ethyl cellulose and stearic acid in different ratios. Kousuke Nakano, et al., *Oral Sustained-Release Cisplatin Preparations for Rats and Mice*, J. Pharm. Pharmacol. 49:485–490 (1997).

There are various methods commonly known for preparing solid dispersions. These include, but are not limited to the melting method, the solvent method and the melting-solvent method.

In the melting method, the physical mixture of a drug in a water-soluble carrier is heated directly until it melts. The melted mixture is then cooled and solidified rapidly while rigorously stirred. The final solid mass is crushed, pulverized and sieved. Using this method a super saturation of a solute or drug in a system can often be obtained by quenching the melt rapidly from a high temperature. Under such conditions, the solute molecule may be arrested in solvent matrix by the instantaneous solidification process. A disadvantage is that many substances, either drugs or carriers, may decompose or evaporate during the fusion process at high temperatures. However, this evaporation problem may be avoided if the physical mixture is heated in a sealed container. Melting under a vacuum or blanket of an inert gas such as nitrogen may be employed to prevent oxidation of the drug or carrier.

The solvent method has been used in the preparation of solid solutions or mixed crystals of organic or inorganic compounds. Solvent method dispersions may prepared by dissolving a physical mixture of two solid components in a common solvent, followed by evaporation of the solvent. The main advantage of the solvent method is that thermal decomposition of drugs or carriers may be prevented because of the low temperature required for the evaporation of organic solvents. However, some disadvantages associated with this method are the higher cost of preparation, the difficulty in completely removing liquid solvent, the possible adverse effect of its supposedly negligible amount of the solvent on the chemical stability of the drug.

Another method of producing solid dispersions is the melting-solvent method. It is possible to prepare solid dispersions by first dissolving a drug in a suitable liquid solvent and then incorporating the solution directly into a melt of polyethylene glycol, obtainable below 70 degrees, without removing the liquid solvent. The selected solvent or dissolved lipoate may be selected such that the solution is not miscible with the melt of polyethylene glycol. The polymorphic form of the lipoate may then be precipitated in the melt. Such a unique method possesses the advantages of both the melting and solvent methods. Win Loung Chiou, et al., *Pharmaceutical Applications of Solid Dispersion Systems*, J. Pharm. Sci. 60:1281–1301 (1971).

Another controlled release dosage form is a complex between an ion exchange resin and the lipoates. Ion exchange resin-drug complexes have been used to formulate sustained-release products of acidic and basic drugs. In one preferable embodiment, a polymeric film coating is provided to the ion exchange resin-drug complex particles, making drug release from these particles diffusion controlled. See Y. Raghunathan et al., *Sustained-released drug delivery system I: Coded ion-exchange resin systems for phenylpropanolamine and other drugs*, J. Pharm. Sciences 70: 379–384 (1981).

Injectable micro spheres are another controlled release dosage form. Injectable micro spheres may be prepared by non-aqueous phase separation techniques, and spray-drying techniques. Micro spheres may be prepared using polylactic acid or copoly(lactic/glycolic acid). Shigeyuki Takada, *Utilization of an Amorphous Form of a Water-Soluble GPIIb/IIIa Antagonist for Controlled Release From Biodegradable Micro spheres*, Pharm. Res. 14:1146–1150 (1997), and ethyl cellulose, Yoshiyuki Koida, *Studies on Dissolution Mechanism of Drugs from Ethyl Cellulose Microcapsules*, Chem. Pharm. Bull. 35:1538–1545 (1987).

Other controlled release technologies that may be used in the practice of this invention are quite varied. They include SODAS, INDAS, IPDAS, MODAS, EFVAS, PRODAS, and DUREDAS. SODAS are multi particulate dosage forms utilizing controlled release beads. INDAS are a family of drug delivery technologies designed to increase the solubility of poorly soluble drugs. IPDAS are multi particulate tablet formation utilizing a combination of high density controlled release beads and an immediate release granulate. MODAS are controlled release single unit dosage forms. Each tablet consists of an inner core surrounded by a semipermeable multiparous membrane that controls the rate of drug release. EFVAS is an effervescent drug absorption system. PRODAS is a family of multi particulate formulations utilizing combinations of immediate release and controlled release mini-tablets. DUREDAS is a bilayer tablet formulation providing dual release rates within the one dosage form. Although these dosage forms are known to one of skill, certain of these dosage forms will now be discussed in more detail.

INDAS was developed specifically to improve the solubility and absorption characteristics of poorly water soluble drugs. Solubility and, in particular, dissolution within the fluids of the gastrointestinal tract is a key factor in determining the overall oral bioavailability of poorly water soluble drug. By enhancing solubility, one can increase the overall bioavailability of a drug with resulting reductions in dosage. INDAS takes the form of a high energy matrix tablet, production of which is comprised of two distinct steps: the adensosine analog in question is converted to an amorphous form through a combination of energy, excipients, and unique processing procedures.

Once converted to the desirable physical form, the resultant high energy complex may be stabilized by an absorption process that utilizes a novel polymer cross-linked technology to prevent recrystallization. The combination of the change in the physical state of the lipoate coupled with the solubilizing characteristics of the excipients employed enhances the solubility of the lipoate. The resulting absorbed amorphous drug complex granulate may be formulated with a gel-forming erodible tablet system to promote substantially smooth and continuous absorption.

IPDAS is a multi-particulate tablet technology that may enhance the gastrointestinal tolerability of potential irritant and ulcerogenic drugs. Intestinal protection is facilitated by the multi-particulate nature of the IPDAS formulation which promotes dispersion of an irritant lipoate throughout the gastrointestinal tract. Controlled release characteristics of the individual beads may avoid high concentration of drug being both released locally and absorbed systemically. The combination of both approaches serves to minimize the potential harm of the lipoates with resultant benefits to patients.

IPDAS is composed of numerous high density controlled release beads. Each bead may be manufactured by a two step process that involves the initial production of a micromatrix with embedded lipoates and the subsequent coating of this micromatrix with polymer solutions that form a rate limiting semipermeable membrane in vivo. Once an IPDAS tablet is ingested, it may disintegrate and liberate the beads in the stomach. These beads may subsequently pass into the duodenum and along the gastrointestinal tract, preferably in a controlled and gradual manner, independent of the feeding state. Lipoate release occurs by diffusion process through the micromatrix and subsequently through the pores in the rate controlling semipermeable membrane. The release rate from the IPDAS tablet may be customized to deliver a drug-specific absorption profile associated with optimized clinical benefit. Should a fast onset of activity be necessary, immediate release granulate may be included in the tablet. The tablet may be broken prior to administration, without substantially compromising drug release, if a reduced dose is required for individual titration.

MODAS is a drug delivery system that may be used to control the absorption of water soluble lipoates. Physically MODAS is a non-disintegrating table formulation that manipulates drug release by a process of rate limiting diffusion by a semipermeable membrane formed in vivo. The diffusion process essentially dictates the rate of presentation of drug to the gastrointestinal fluids, such that the uptake into the body is controlled. Because of the minimal use of excipients, MODAS can readily accommodate small dosage size forms. Each MODAS tablet begins as a core containing active drug plus excipients.

This core is coated with a solution of insoluble polymers and soluble excipients. Once the tablet is ingested, the fluid of the gastrointestinal tract may dissolve the soluble excipients in the outer coating leaving substantially the insoluble polymer. What results is a network of tiny, narrow channels connecting fluid from the gastrointestinal tract to the inner drug core of water soluble drug. This fluid passes through these channels, into the core, dissolving the drug, and the resultant solution of drug may diffuse out in a controlled manner. This may permit both controlled dissolution and absorption. An advantage of this system is that the drug releasing pores of the tablet are distributed over substantially the entire surface of the tablet. This facilitates uniform drug absorption reduces aggressive unidirectional drug delivery. MODAS represents a very flexible dosage form in that both the inner core and the outer semipermeable membrane may be altered to suit the individual delivery requirements of a drug. In particular, the addition of excipients to the inner core may help to produce a microenvironment within the tablet that facilitates more predictable release and absorption rates. The addition of an immediate release outer coating may allow for development of combination products.

Additionally, PRODAS may be used to deliver lipoates according to the invention. PRODAS is a multi particulate drug delivery technology based on the production of controlled release mini tablets in the size range of 1.5 to 4 mm in diameter. The PRODAS technology is a hybrid of multi particulate and hydrophilic matrix tablet approaches, and may incorporate, in one dosage form, the benefits of both these drug delivery systems.

In its most basic form, PRODAS involves the direct compression of an immediate release granulate to produce individual mini tablets that contain lipoates. These mini tablets are subsequently incorporated into hard gels and capsules that represent the final dosage form. A more beneficial use of this technology is in the production of controlled release formulations. In this case, the incorporation of various polymer combinations within the granulate may delay the release rate of drugs from each of the individual mini tablets. These mini tablets may subsequently be coated with controlled release polymer solutions to provide additional delayed release properties. The additional coating may be necessary in the case of highly water soluble drugs or drugs that are perhaps gastroirritants where release can be delayed until the formulation reaches more distal regions of the gastrointestinal tract. One value of PRODAS technology lies in the inherent flexibility to formulation whereby combinations of mini tablets, each with different release rates, are incorporated into one dosage form. As well as potentially permitting controlled absorption over a specific period, this also may permit targeted delivery of drug to specific sites of absorption throughout the gastrointestinal tract. Combination products also may be possible using mini tablets formulated with different active ingredients.

DUREDAS is a bilayer tableting technology that may be used in the practice of the invention. DUREDAS was developed to provide for two different release rates, or dual release of a drug from one dosage form. The term bilayer refers to two separate direct compression events that take place during the tableting process. In a preferable embodiment, an immediate release granulate is first compressed, being followed by the addition of a controlled release element which is then compressed onto this initial tablet. This may give rise to the characteristic bilayer seen in the final dosage form.

The controlled release properties may be provided by a combination of hydrophilic polymers. In certain cases, a rapid release of the lipoic acid may be desirable in order to facilitate a fast onset of therapeutic affect. Hence one layer of the tablet may be formulated as an immediate release granulate. By contrast, the second layer of the tablet may release the drug in a controlled manner, preferably through the use of hydrophilic polymers. This controlled release may result from a combination of diffusion and erosion through the hydrophilic polymer matrix.

A further extension of DUREDAS technology is the production of controlled release combination dosage forms. In this instance, two different lipoic acid compounds may be incorporated into the bilayer tablet and the release of drug from each layer controlled to maximize therapeutic affect of the combination.

The α-lipoic acid of the invention can be incorporated into any one of the aforementioned controlled released dosage forms, or other conventional dosage forms. The amount of α-lipoic acid contained in each dose can be adjusted, to meet the needs of the individual patient, and the indication. One of skill in the art and reading this disclosure will readily recognize how to adjust the level of α-lipoic acid and the release rates in a controlled release formulation, in order to optimize delivery of α-lipoic acid and its bioavailability.

THERAPEUTIC INDICATIONS

The controlled release lipoic acid formulations of the present invention can be used to obtain a wide range of desirable effects. Particularly the formulations of the invention are useful in treating essentially any disease state or symptom which is treatable by long term administration of antioxidants. Further, the invention can be used in the treatment of diseases which involve carbohydrate metabolism and blood glucose disposal which includes various forms of diabetes. Further, the invention is useful in the treatment of various adverse effects on the eyes and skin when the adverse effect are due to high levels of free radicals which can be dissipated by the presence of antioxidants or high levels of serum glucose which can be reduced by stimulating basal glucose transport. Maintaining substantially constant levels of lipoic acid provides a long term antioxidant effect which assists in immunomodulation and can result in improved liver and kidney function. Because of the long term antioxidant effect in the circulatory system the present invention has a variety of beneficial effects on the cardiovascular system and in the alleviation of certain liver diseases as well as neurodegenerative diseases. A patient infected with HIV can benefit from the enhanced effect obtained on the immune system.

The data provided here do not show specific treatments of many of the diseases or symptoms mentioned above. However, the invention is believed to be responsible for obtaining a wide range of beneficial effects particularly when the controlled release formulation is administered to patient'sover long periods of time, i.e. weeks, months and years. By maintaining substantially constant levels of lipoic acid in the blood over very long periods of time a range of desirable physiological results are obtained. Stated differently by continually maintaining the constant serum levels of the powerful antioxidant and keeping a patient'sblood glucose level within a more desirable range the adverse effects obtained from free radicals and high fluctuating glucose levels are avoided.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

In a first step, racemic α-lipoic acid is screened to a particle size range of 150 to 450 microns. The racemic α-lipoic acid is then added to a Glatt (Ramsey, N.J.) fluid bed granulator. The racemic α-lipoic acid particles become the cores for a coated particle. The cores are coated with a 30% w/w aqueous dispersion of EUDRAGIT® (NE30 D, methacrylic acid ester) and talc. This yields coated particles with a dried coating weight equal to about 10% of the total weight of the coated particle. The inlet air temperature is kept at a temperature of 25 deg C. After drying, the coated particles are screened using a 40 mesh screen.

The resulting, free-flowing particles are then blended and directly compressed using a tableting press according to the following formula:

Racemic α-lipoic acid, coated particles 81%
METHOCEL® K100 10%
(methylcellulose)
Microcrystalline cellulose 5%
Stearic Acid 3%
Micronized silica 0.5%
Magnesium Stearate 0.5%

The resulting tablet is a sustained release formulation.

Example 2

In a first step, R–(+)-α-lipoic acid is screened to a particle size range of 150 to 450 microns. The R–(+)-α-lipoic acid is then added to a Glatt (Ramsey, N.J.) fluid bed granulator. The R–(+)-α-lipoic acid particles become the cores for a coated particle. The cores are coated with a 30% w/w aqueous dispersion of EUDRAGIT® (NE30 D, methacrylic acid ester) and talc. This yields coated particles with a dried coating weight equal to about 10% of the total weight of the coated particle. The inlet air temperature is kept at a temperature of 25 deg C. After drying, the coated particles are screened using a 40 mesh screen.

The resulting, free-flowing particles are then blended and directly compressed using a tableting press according to the following formula:

R–(+)-α-lipoic acid, coated particles 81%
METHOCEL® K100 10%
(methylcellulose)
Microcrystalline cellulose 5%
Stearic Acid 3%
Micronized silica 0.5%
Magnesium Stearate 0.5%

The resulting tablet is a sustained release formulation.

Example 3

In a first step, R–(+)-α-lipoic acid is screened to a particle size range of 150 to 450 microns. The R–(+)-α-lipoic acid is then added to a Glatt (Ramsey, N.J.) fluid bed granulator. The R–(+)-α-lipoic acid particles become the cores for a coated particle. EUDRAGIT® (L/S 100, methacrylic acid ester) is dissolved in isopropyl alcohol to form a 15% w/w solution. Triethyl citrate, talc, and water are additionally added to the solution. Total solids content of the resulting mixture is 9.6% w/w. This yields coated particles with a dried coating weight equal to about 10% of the total weight of the coated particle. The inlet air temperature is kept at a temperature of 25 deg C. After drying, the coated particles are screened using a 40 mesh screen.

The resulting, free-flowing particles are then blended and directly compressed using a tableting press according to the following formula:

R–(+)-α-lipoic acid, coated particles 81%
METHOCEL® K100 5%
(methylcellulose)
Microcrystalline cellulose 5%
Stearic Acid 3%
Micronized silica 0.5%
Magnesium Stearate 0.5%

The resulting tablet is protected from the harsh acid environment of the stomach, and is delivered to the small intestine where it is gradually released.

Example 4

In a first step, racemic α-lipoic acid is screened to a particle size range of 150 to 450 microns. The racemic α-lipoic acid is then added to a Glatt (Ramsey, N.J.) fluid bed granulator. The racemic α-lipoic acid particles become the cores for a coated particle. EUDRAGIT® (L/S 100, methacrylic acid ester) is dissolved in isopropyl alcohol to form a 15% w/w solution. Triethyl citrate, talc, and water are additionally added to the solution. Total solids content of the resulting mixture is 9.6% w/w. This yields coated particles with a dried coating weight equal to about 10% of the total weight of the coated particle. The inlet air temperature is kept at a temperature of 25 deg C. After drying, the coated particles are screened using a 40 mesh screen.

The resulting, free-flowing particles are then blended and directly compressed using a tableting press according to the following formula:

Racemic α-lipoic acid, coated particles 81%
METHOCEL® K100 10%
(methylcellulose)
Microcrystalline cellulose 5%
Stearic Acid 3%
Micronized silica 0.5%
Magnesium Stearate 0.5%

The resulting tablet is protected from the harsh acid environment of the stomach, and is delivered to the small intestine where it is gradually released.

Example 5

A preblend of 98% w/w CARBOPOL® 934 (B. F. Goodrich Chemical, lightly cross-linked acrylic acid allyl sucrose copolymer) and 2% w/w micronized silica is prepared. To this mixture, racemic α-lipoic acid, METHOCEL® K100, stearic acid, and lactose are added according to the following formula:

Racemic α-lipoic acid preblend 70%
CARBOPOL® 934/silica preblend 10%
METHOCEL® K100 10%
stearic acid 5%
lactose 5%

The resulting mixture is tableted using a direct compression tableting press to form a bioadhesive formulation.

Example 6

A preblend of 98% w/w R–(+)-α-lipoic acid and 2% w/w CAB-O-SIL® micronized silica is formed. To this mixture is added guar gum (AQUALON ® G-3), polyvinylpyraolidone (PVP), calcium carbonate, stearic acid, lactose, and magnesium stearate in the following amounts:

R–(+)-α-lipoic acid/CAB-O-SIL® blend 49.5%
guar gum (AQUALON® G-3) 30%
polyvinylpyraolidone (PVP) 5%
calcium carbonate 5%
stearic acid 5%
lactose 5%
magnesium stearate 0.5%

The resulting mixture is tableted using a direct compression tableting press to form a sustained release caplet formulation.

Example 7

| Item No. | Item Description | Percent | Theoretical Quantity | Unit of Measure |
|---|---|---|---|---|
| 1. | α-Lipoic Acid | 60 | 4800.0 | g |
| 2. | Microcrystalline Cellulose, NF (Avicel PH 101) | 18 | 1440.0 | g |
| 3. | Aquacoat CPD (30% w/w) | 15* | 4000.0* | g |
| 4. | Povidone K29/32, USP | 3 | 240.0 | g |
| 5. | Carbopol 974P | 2.5 | 200.0 | g |
| 6. | Talc, USP | 1 | 80.0 | g |
| 7. | Magnesium Stearate, NF | 0.5 | 40.0 | g |
| 8. | Purified Water, USP | | — | g |
| N/A | TOTAL | 100 | 8000.0 | g |

*Quantity indicates amount of dispersion to be used in granulating. Actual Solids Content-1200 g - 15% is based on solids content Before formulating a check should be made of the room and equipment in order to verify that the cleaning procedure has been performed and approved. Weigh and charge α-Lipoic Acid (Item 1) and Avicel PH 101, (Item 2) in a Hobart Mixer and mix for two (2) minutes with the mixer speed set at 1 or 2. Granulate the Step 2 material by slowly adding Aquacoat CPD (Item 3) until granules are formed. Add additional Purified Water, USP (Item 8) if required, and mix until the granules are formed. Mixer Speed Setting remains at 1–2. Spread the granulation evenly from Step 3 on paper-lined trays and load them into the oven. Dry at 40° C.±5°C. for two (2) hours. Check LOD and record moisture content. If LOD is more than 2%, continue drying until LOD is below 2%. Pass the dried material from Step 5 through a size 14 mesh screen, hand held or using a Quadro Comil. Charge the Step 6 granulation into a V-blender. Charge the Step 7 blend in blender with Povidone K29/32, USP (Item 4) and Carbopol 974P (Item 5) and mix for five (5) minutes. Charge the V-blender with Talc (Item 6) and Magnesium Stearate, NF (Item 7) and blend for three (3) minutes. Empty the blend from the V-blender into a properly labeled tared PE-lined container and record the weights in Step 11. Theoretical weight of blend: 8000.0 g. Lower Limit 95% and Upper Limit 102%. Any discrepancy from these established limits must be reported to Production and Quality Assurance. Any discrepancy must be appropriately investigated and documented. Hold the blend in the in-process Q.C. Hold area for further processing. Using the amounts shown above will result in sufficient formulations to produce above 16,000 300 mg tablets.

Example 8

A controlled release oral dosage form of racemic α-lipoic acid was administered to a group of volunteers. Each dose consisted of a tablet containing 300 mg of racemic α-lipoic acid, compounded with calcium phosphate, starch, cellulose ethers, polycarboxylic acid, and magnesium stearate. The 300 mg tablets used with these patients were tablets prepared in a manner as described above in Example 7. Each patient was given two 300 mg tablets in the morning before eating and one 300 mg tablet within 6 to 8 hours.

The results were as follows:

| | | | Average Glucose Levels | |
|---|---|---|---|---|
| Patient No. | Sex (M/F) | Age | Before | After |
| 1 | M | 47 | 240 | 150 |
| 2 | F | 46 | 225 | 120 |
| 3 | M | 45 | 155 | 130 |
| 4 | M | 67 | 155 | 95 |
| 5 | F | 47 | 175 | 195 |
| 6 | M | 82 | 138 | 129 |
| 7 | M | 48 | 174 | 119 |
| 8 | M | 71 | 150 | 90 |

As can be seen from Table 1, the average glucose level before treatment with the controlled release lipoic acid was 176.5 mg/dl. After treatment with the controlled release lipoic acid, the average glucose level was 128.5 mg/dl, a average decrease of 48 mg/dl.

Example 9

A controlled release oral dosage form of racemic α-lipoic acid was administered to a group of volunteers. Each dose consisted of a tablet containing 300 mg of racemic α-lipoic acid, compounded with calcium phosphate, starch, cellulose ethers, polycarboxylic acid, and magnesium stearate. The 300 mg tablets used with these patients were tablets prepared in a manner as described above in Example 7 and dosed in the same manner described in Example The results were as follows:

| | | | Average Glucose Levels | |
|---|---|---|---|---|
| Patient No. | Sex (M/F) | Age | Before | After |
| 1 | M | 62 | 400 | 140 |
| 2 | F | 65 | 300 | 149 |
| 3 | F | 51 | 325 | 185 |

As can be seen from Table 2, the average glucose level before treatment with the controlled release lipoic acid was 342 mg/dl. After treatment with the controlled release lipoic acid, the average glucose level was 158 mg/dl, a average decrease of 184 mg/dl.

Example 10

Fourteen human volunteers described below were administered controlled release lipoic acid formulations of the present invention. The formulations were prepared in a manner such as that described in Example 7 above. Each patient was dosed with two 300 mg tablets in the morning before eating and one 300 mg tablet approximately six hours thereafter. In some instances some patients were dosed with additional medications as indicated. These results demonstrate the improved results with the lipoic acid controlled release formulations of the invention alone or in combination with other pharmaceutically active compositions.

New CR ALA Tablet Study
30-Nov-98

| Patient # | Type | Description | Age | Average Glucose Levels | | Percent | Comments |
| | | | | Before | After | Change | Change | |
| --- | --- | --- | --- | --- | --- | --- | --- | --- |
| 1 | Type 2 | Glucophage 850 mg 3x | 51 | 220 | 110 | −110 | −50% | |
| 2 | type 2 | Insulin/Glucophage | 70 | 168 | 112 | −56 | −33% | |
| 3 | Type 2 | Insulin/Oral Meds | 54 | 175 | 120 | −55 | −31% | Cut meds in half and 9 to 7 AlC |
| 4 | Type 2 | Glucophage 500 mg 2x Day | 65 | 135 | 114 | −21 | −16% | |
| 6 | type 2 | Diet & Exercise | 46 | 189 | 131 | −58 | −31% | Dr. did not have to put on drugs and drop AlC from 8.3 to 6.2 |
| 7 | Type 2 | Glucophage XL | 67 | 135 | 90 | −45 | −33% | |
| 8 | Type 2 | Insulin/Glucophage | 46 | 300 | 200 | −10 | −33% | |
| 10 | Type 2 | Insulin/Oral Meds | 72 | 185 | 135 | −50 | −27% | |
| 11 | Type 2 | Insutin | 72 | 135 | 87 | −48 | −36% | |
| 12 | Type 2 | Glucophage/Glucotrol | 79 | 225 | 140 | −85 | −38% | |
| 13 | Type 2 | Diet & Exercise | 59 | 145 | 111 | −35 | −24% | |
| 14 | Type 2 | "Insulin, 15 unix 2x" | 51 | 325 | 191 | −134 | −41% | |
| | | AVERAGE = | | 186 | 128 | −57 | −29% | |
| 5 | Normal | Severe polyneuropathy | #N/A | #N/A | #N/A | #N/A | #N/A | Eliminated all neuropath |

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

What is claimed is:

1. An oral dosage for mnulation, comprising:
   a therapeutically effective amount of lipoic acid; and
   an excipient material;
   wherein the formulation is characterized by
   (a) protecting the lipoic acid from chemical degradation in a patient's gastrointestinal tract;
   (b) releasing the lipoic acid in a controlled manner; and
   releasing lipoic acid in a manner such that lipoic acid is maintained in a patient's circulatory system at a therapeutic level for a period of about four hours or more.

2. The formulation of claim 1, comprising:

| | |
| --- | --- |
| lipoic acid | 60% by weight ± 10% |
| excipient material | 40% by weight ± 10%. |

3. The formulation of claim 1, wherein the releasing in a controlled manner is characterized by a period of a continually decreasing rate of release until all active ingredient has been released.

4. The formulation of claim 1, wherein the lipoic acid is released over a period of six hours or more.

5. The formulation of claim 2, wherein the excipient material comprises cellulose acetate phthalate aqueous dispersion and microcrystalline cellulose.

6. The formulation of claim 1, further characterized by having a rate of release upon oral administration which is gradual and continually decreasing over a period of time in a manner which allows for maintaining a substantial constant level of the lipoic acid in blood serum of a patient ingesting the formulation.

7. The formulation of claim 1, further comprising an orally active antidiabetic selected from the group consisting of a sulfonylurea, a biguanide and a thiazolidinedione.

8. The formulation of claim 1, further comprising metformin hydrochloride.

9. The formulation of claim 1, comprising:

| | |
| --- | --- |
| lipoic acid | 60% by weight ± 10% |
| microcrystalline cellulose | 14% by weight ± 10% |
| cellulose acetate phthalate aqueous dispersion | 15% by weight ± 10% |
| polyvinylpyraolidone | 3% by weight ± 10% |
| ethyl acetate | 2.5% by weight ± 10% |
| hydrous magnesium silicate | 1% by weight ± 10% |
| carboxy methyl ether | 4% by weight ± 10% |
| magnesium stearate | 0.5% by weight ± 10%. |

10. The formulation of claim 1, comprising:

| | |
| --- | --- |
| lipoic acid | 60% by weight ± 2% |
| microcrystalline cellulose | 14% by weight ± 2% |
| cellulose acetate phthalate aqueous dispersion | 15% by weight ± 2% |
| polyvinylpyraolidone | 3% by weight ± 2% |
| ethyl acetate | 2.5% by weight ± 2% |
| hydrous magnesium silicate | 1% by weight ± 2% |
| carboxy methyl ether | 4% by weight ± 2% |
| magnesium stearate | 0.5% by weight ± 2%. |

11. The formulation of claim 1, wherein the lipoic acid is present as a racemic mixture.

12. The formulation of claim 1, wherein the lipoic acid is present as substantially pure R–(+) enantiomer.

13. The formulation of claim 1, wherein the lipoic acid comprises 50% to 70% by weight of the total formulation.

14. The formulation of claim 1, wherein the lipoic acid comprises 60%±2.5% by weight of the total formulation.

15. The formulation of claim 1, wherein the releasing of the lipoic acid is at a rate of about 25 % or less per hour.

16. A method of treating a human patient, comprising:

administering to a human patient a controlled release formulation of lipoic acid which formulation is characterized by maintaining a therapeutic level of lipoic acid in the patient's circulatory system over a period of four hours or more per day; and repeating the administering on three or more consecutive days thereby maintain a therapeutic level of lipoic acid in the patient's circulatory system for four hours or more on three or more consecutive days.

17. The method of claim 16, wherein the therapeutic level is maintained over a period of six hours or more per day and further wherein the repeating is over seven or more consecutive days.

18. A method of reducing a human patient's serum glucose level, comprising:

administering a therapeutically effective amount of an orally active antidiabetic selected from the group consisting of a sulfonylurea, a biguanide and a thiazolidinedione;

administering a controlled release formulation of lipoic acid which formulation is characterized by maintaining a therapeutic level of lipoic acid in the patient's circulatory system over a period of four hours or more per day.

19. The method of claim 18, further comprising:

repeatedly administering the antidiabetic and the lipoic acid on a daily basis for three or more days.

20. The method of claim 19, wherein the antidiabetic is metformin hydrochloride which is administered in an amount in a range of about 500 mg to about 1,000 mg per day.

* * * * *